(12) United States Patent
McNeal-Burgess et al.

(10) Patent No.: US 11,112,181 B2
(45) Date of Patent: Sep. 7, 2021

(54) BODY COOLING SYSTEM

(71) Applicant: FRIA, LLC, Avenel, NJ (US)

(72) Inventors: Sheilisa McNeal-Burgess, Avenel, NJ (US); Karen Ann Webster, New York, NY (US)

(73) Assignee: FRIA, LLC, Avenel, NJ (US)

( * ) Notice: Subject to any disclaimer, the term of this patent is extended or adjusted under 35 U.S.C. 154(b) by 49 days.

(21) Appl. No.: 16/390,611

(22) Filed: Apr. 22, 2019

(65) Prior Publication Data

US 2020/0333079 A1 Oct. 22, 2020

(51) Int. Cl.
- *F28C 3/08* (2006.01)
- *F25D 7/00* (2006.01)
- *F24F 6/04* (2006.01)

(52) U.S. Cl.
CPC ............ *F28C 3/08* (2013.01); *F24F 6/04* (2013.01); *F25D 7/00* (2013.01)

(58) Field of Classification Search
CPC ........... A61F 2007/0214; A61F 7/106; A61F 2007/0058; A61F 2007/0067; A41D 13/0053; A41D 20/005
See application file for complete search history.

(56) References Cited

U.S. PATENT DOCUMENTS

| | | | | |
|---|---|---|---|---|
| 5,157,788 A * | 10/1992 | Schultz | .................... | A42B 1/04 2/195.1 |
| 2005/0118383 A1* | 6/2005 | Cargill | .................... | A61F 7/02 428/68 |
| 2011/0106227 A1* | 5/2011 | Desiderio | ................. | A61F 7/02 607/111 |
| 2014/0081361 A1* | 3/2014 | Dhayan | .................... | A61F 7/10 607/109 |
| 2014/0130687 A1* | 5/2014 | Shibusawa | .............. | C23C 16/26 101/127 |
| 2016/0250373 A1* | 9/2016 | Munro | .................... | A61L 15/26 602/48 |
| 2019/0307604 A1* | 10/2019 | Ainslie | .................... | C25B 1/12 |

OTHER PUBLICATIONS

Asada Hard Mesh, https://asada-mesh.co.jp/en/products/hardmesh_type_ms.html, Oct. 1, 2017.*

* cited by examiner

*Primary Examiner* — Elizabeth J Martin
(74) *Attorney, Agent, or Firm* — Ichthus International Law PLLC

(57) ABSTRACT

A body cooling system including a housing having a top portion, side portions, and a bottom portion. The top portion and the bottom portion include at least one opening. Additionally, the body cooling system includes at least one mesh layer and an absorbent layer at least partially surrounded by the mesh layer.

16 Claims, 5 Drawing Sheets

BODY COOLING SYSTEM

FIELD OF THE INVENTION

The present disclosure generally relates to an apparatus for a body cooling system. More particularly, the present disclosure relates to an apparatus to counteract hot flashes.

BACKGROUND OF THE INVENTION

Presently, to counteract hot flashes that women experience after a certain age includes hormone replacement therapy and herbal supplements. Hormone replacement therapy is controversial and fraught with side effects. However, although this is not a truly safe option, given that presently there are no other choices that are as effective, many women opt to go under hormone replacement therapy. The herbal supplements are somewhat effective but must be consistently taken to have any significant results. Furthermore, there is a good deal of trial and error as there are a variety of supplements on the market and finding the one that works can be very time consuming and frustrating. Moreover, most people do not particularly enjoy taking pills.

SUMMARY OF THE INVENTION

In an aspect, a body cooling system is provided. The body cooling system including a housing including a top portion, side portions, and a bottom portion, wherein the top portion and the bottom portion include at least one opening; at least one mesh layer; and an absorbent layer at least partially surrounded by the mesh layer.

In an aspect, the housing of the body cooling system includes a heat conductive material.

In another aspect, the at least one opening in the top portion of the housing is in fluid contact with ambient air.

In a further aspect, the at least one opening in the bottom portion of the housing includes at least a portion of at least one of the at least one mesh layer and the absorbent layer.

In yet another aspect, the top portion of the housing includes an ornamental design.

In an aspect, the mesh layer comprises a hydrophobic coating.

In a further aspect, the hydrophobic coating in on a side of the mesh layer facing the absorbent layer.

In an aspect, the hydrophobic coating comprises silane.

In an aspect, the silane is Trimethoxy(1H,1H,2H,2H-perfluorodecyl)silane.

In another aspect, the mesh layer includes a mesh size of from about 50 by 50 to about 250 by 250.

In a further aspect, the mesh layer includes a mesh size of about 100 by 100.

In yet another aspect, the mesh includes from about 10% opening to about 50% opening.

In an aspect, the mesh includes about 30% opening.

In another aspect, the mesh is made of a material having anti-bacterial characteristics.

In a further aspect, the mesh is made of at least one of copper, silver, and stainless steel.

In yet another aspect, the mesh is made of 304 stainless steel mesh.

In an aspect, the absorbent material has at least 100% absorbing capacity.

In another aspect, the absorbent material comprises polypropylene.

In a further aspect, the absorbent material comprises at least one of polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

In yet another aspect, the absorbent material is a hydrogel.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

The present disclosure in its several aspects and embodiments can be more fully understood from the detailed description and the accompanying drawings, wherein.

Throughout this specification and figures like reference numbers identify like elements.

DETAILED DESCRIPTION OF THE INVENTION

It is to be understood that both the foregoing general description and the following detailed description are exemplary and explanatory only, and are intended to provide an explanation of various embodiments of the present teachings.

Active cooling involves cooling technologies that rely on an externally powered device for heat transfer. It usually involves forced convection to optimize heat removal and thermal management. They are commonly integrated into electronics, which act as the feedback system for maintaining thermal conditions. The primary disadvantage of active thermal management is that it requires power or electricity, in the form of batteries, therefore resulting in much higher costs. Additionally, these extra components increase the size and weight of the entire device.

A new approach is needed to create a cooling system that utilizes passive cooling that is reliable with a controlled cooling rate. To this end, in an example, the cooling system can include a mesh having a hydrophobic material or composition deposited thereon and an absorbent in communication with the mesh. This exemplary design enables the cooling system to achieve lowering the human body temperature from about 1° C. to about 10° C., such as by approximately 5° C.

Evaporation of liquid, especially water, requires absorbing a very large amount of heat from the surroundings. Thus, most passive systems are unable to control the cooling rate (i.e., evaporation of the liquid). However, sandwiching the absorbent or membrane between two mesh members having a hydrophobic coating can control the rate of evaporation. In an example, the mesh members can be coated by any known method, such as vapor deposition. The hydrophobic coating can trap the liquid in the absorbent member, thus, reducing the evaporation rate.

Figure 1:
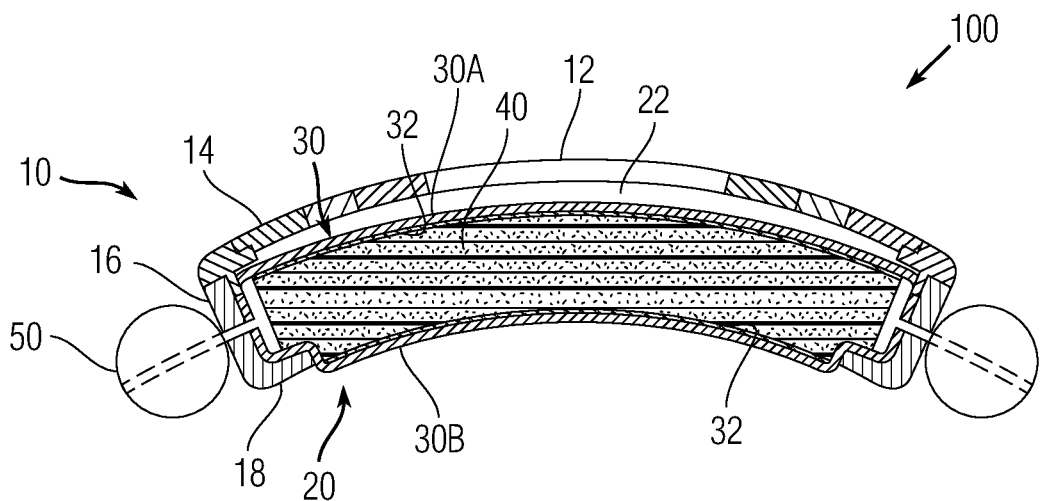
FIG. 1 is a cross-sectional view of a body cooling system, according to an example of the present disclosure.

In an example, as shown in FIG. 1, the cooling system 100 can include a housing 10, at least one mesh layer 30, and an absorbent layer 40. In an example, the mesh layer 30 and the absorbent layer 40 can be positioned inside the housing 10.

Figure 2:
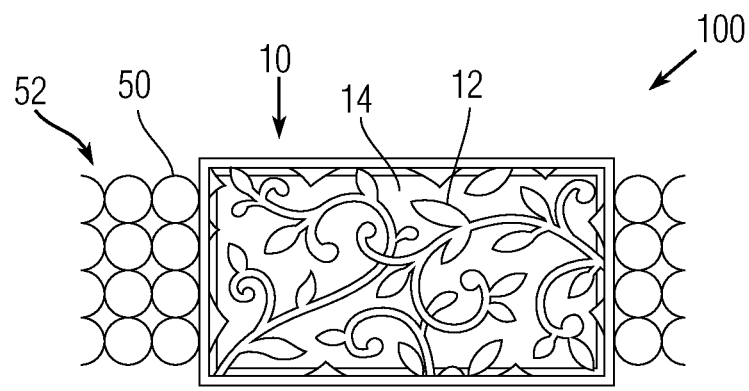
FIG. 2 is a top view of the cooling system of FIG. 1, according to an example of the present disclosure.
Figure 3:
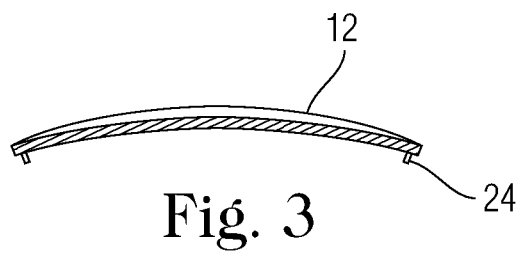
FIG. 3 is a side view of the top plate portion of the body of the cooling system of FIG. 1, according to an example of the present disclosure.

Referring to FIGS. 1-3, the housing 10 can include a top portion/plate 12, side portions 16, and a bottom portion 18. The top portion/plate 12 can include a design having at least one opening 14 for air to come in contact with the content of the housing 10.

Figure 4:
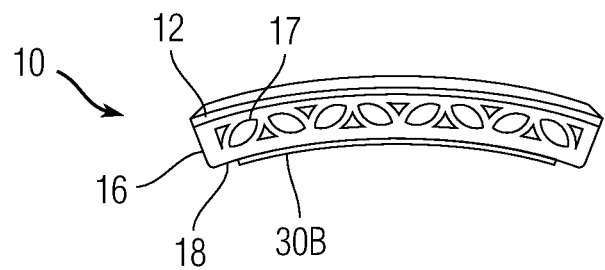
FIG. 4, is a side view of the cooling system of FIG. 1, according to an example of the present disclosure.

In an example, the side portions 16 can also include at least one opening 17 (see FIG. 4). Similar to the at least one opening 14 in the top portion/plate 12, the at least one opening 17 on the side portions 16 can be arranged such that the at least one opening 17 can create an ornamental design on the side of the housing 10.

In an example, the bottom portion 18 can include at least one opening 20. The at least one opening 20 can be a single opening or can be a plurality of openings. The at least one opening 20 can be facing a portion of the skin of the user of the cooling system 100.

In one example, as shown in FIG. 2, the at least one opening 14 on the top portion/plate 12 of the housing 10 can be arranged such that the at least one opening 14 creates an ornamental design that may be pleasant to a potential customer. In this example, the cooling system 100 can be worn like a charm bracelet, having a band 52. The band 52 can be made of any material and can include any design. For example, the band 52 can include one or more strings of spheres 50, to make the band 52 look like a band made of pearls.

In an example, the top portion/plate 12 is removably connected to the housing 10, such that a user can access the content of the housing 10. For example, the top portion/plate 12 can include a hinge on one side so that a user can open and close the top portion/plate 12 to replace or repair the mesh layer 30 and or the absorbent layer 40. In another example, the top portion/plate 12 can be friction fitted or can be snapped into the housing 10. Having a top portion/plate 12 that is friction fitted or can be snapped into the housing 10 can be advantageous because the user can interchange the top portion/plate 12 with other plates that have different designs due to the position of or patterns created by the at least one opening 14. Thus, depending on the occasion, a user can exchange the top portion/plate 12 as deemed necessary.

The housing 10 and the band 52 of the cooling system 100 can be made of any materials. In one example, the housing 10 and the band 52 are made of materials that are thermally conductive. Such materials include, but are not limited to, diamond, silver, copper, gold, aluminum, magnesium, sodium, graphite, tungsten, beryllium, zinc, nickel, steel, tantalum, stainless steel, and/or alloys thereof. The housing can also be made of a material that has an anti-bacterial effect. Such materials include, but are not limited to, silver, copper, and their alloys (brasses, bronzes, cupronickel, copper-nickel-zinc, and others). Additionally, in an example, the housing 10 can include an antibacterial, antivirus, and or antifungal coating. Such a coating can include but is not limited to, organosilane coating.

In an example, the housing 10 can retain a mesh layer 30 and an absorbent layer 40. The mesh layer 30 can be made of any material with any mesh and wire size. The mesh size determines the flexibility of the mesh layer 30 and the openings to provide sufficient contact or access to the environment/air. For example, the mesh size can be from about 50×50 or less to about 250×250 or more. For example, the mesh size can be about 100×100. Additionally, the openings in the mesh layer 30 can encompass from about 10% or less of the material to about 50% or more. For example, the openings in the mesh layer 30 can encompass about 30% of the material.

In an example, the mesh layer 30 can be made of any material. For example, the mesh layer 30 can be made of same or different material from the housing 10. In one example, the mesh layer 30 is also made of thermally conductive materials, such as silver, copper, gold, aluminum, magnesium, sodium, graphite, tungsten, beryllium, zinc, nickel, steel, tantalum, or a combination thereof. Alternatively and/or additionally it can be made of a material, such as stainless steel. For example, the mesh layer 30 can be made of 304 stainless steel. The mesh layer 30 can also be made of materials having an anti-bacterial effect. For example, the mesh layer can be made of silver, copper, and their alloys (brasses, bronzes, cupronickel, copper-nickel-zinc, and others). Furthermore, the mesh layer 30 can include an antibacterial, antivirus, and or antifungal coating. Such a coating can be, for example, an organosilane coating.

The mesh layer 30 can include a hydrophobic coating 32. In one example, the hydrophobic coating 32 is placed on both sides of the mesh layer 30. In another example, the hydrophobic coating is placed on a portion of the surface of the mesh layer 30 that is facing the absorbent layer 40. By sandwiching the absorbent layer 40 between the mesh layer 30 having a hydrophobic coating 32 on the surface facing the absorbent layer 40 the evaporation rate can be controlled.

The hydrophobic coating 32 can be any chemical with low surface energy that can form a uniform coating on the surface of the mesh layer 30. In an example, the hydrophobic coating 32 can be a silane coating, such as Trimethoxy(1H,1H,2H,2H-perfluorodecyl)silane (HTMS).

The silane can be deposited on the mesh layer 30 by any known methods. For example, the silane can be deposited by chemical vapor deposition (CVD). The silane can be mixed with a solvent, such as toluene. In one example, the ratio of the silane to a solvent can be from about 15 to 0.1 to about 5 to 2, such as about 9.5 to 0.5 by volume. In one example, the mixed silane and solvent along with the surface of the mesh layer 30 to be coated can be left in a closed container at a predetermined temperature for a predetermined time.

For example, the temperature can be from about 70° C. to about 120° C., such as about 90° C. for a time of from about 10 hours to about 1 hour or less, such as about 3 hours.

In one example, the mesh layer 30 covers the top portion of the absorbent layer 40. In another example, the mesh layer 30 at least partially encapsulates the absorbent layer 40. When the mesh layer 30 at least partially encapsulates the absorbent layer 40, the mesh layer 30 can include two mesh layers, such as mesh layers 30A and 30B. For example, a first mesh layer 30A can cover at least a portion of the top surface of the absorbent layer 40 and a second mesh layer 30B can cover at least a portion of the bottom surface of the absorbent layer 40. In one example, the ends of each of the first and second mesh layers 30A and 30B can be connected to one another by adhesion. In another example, a single mesh layer 30 can at least partially encapsulate the absorbent layer 40.

Figure 5:
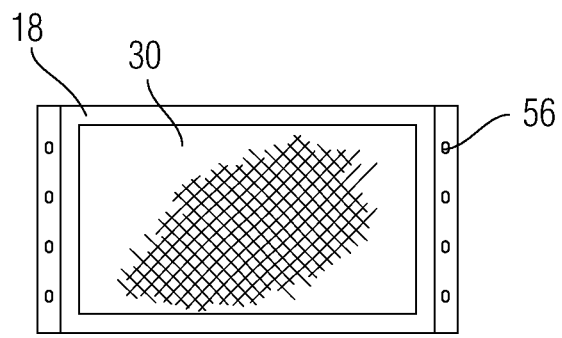
FIG. 5 is a bottom view of the cooling system of FIG. 1, according to an example of the present disclosure.

Referring to FIG. 1, in one example, when the absorbent layer 40 and the mesh layer 30 are placed in the housing, space 22 can be formed between the mesh layer 30 and the top portion/plate 12. This space allows air to circulate and to better dissipate the heat from the absorbent layer 40. In contrast, as shown in FIGS. 1 and 4, the mesh layer positioned at the bottom of the housing is in direct contact with the user's skin/body part. Thus, in this example, the mesh layer 30 at the bottom portion 18 of the housing 10 can protrude out of the at least one opening 20 and extend out of the bottom portion 18. Alternatively, as shown in FIG. 5, the mesh layer 30, at the bottom portion 18 of the housing 10, can protrude out of the at least one opening 20, such that the mesh layer 30 is substantially flushed with the bottom portion 18 of the housing 10.

In an example, the absorbent layer 40 that may be sandwiched between one or more mesh layers 30. The absorbent material can be any commercially available absorbent. In one example, the absorbent material has at least 100% absorbing capacity, such as at least 150% absorbing capacity. The absorbent layer 40 can be made of a polymer, such as polypropylene. Some exemplary absorbing materials that can be used as the absorbent layer 40 include, but are not limited to, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The absorbent layer can also be made of a hydrogel.

In use, a user can place the cooling system 100 on her wrist, arm, neck or any other body part. Once the cooling system 100 is worn by the user, the user can apply a liquid, such as water or alcohol to the absorbent layer 40. As shown in FIG. 1, the mesh layer 30 on the top surface of the absorbent layer 40 is open to ambient atmosphere, which results in gradual evaporation of the liquid in the absorbent layer 40. The mesh layer 30 located at the bottom portion 18 of the housing 10 can be in contact with the human skin. As a result, heat from the human skin can be conducted to the mesh layer 30 and the absorbent layer 40. As the heat is transferred from the skin to the absorbent layer 40, the heated liquid in the absorbent layer 40 can be evaporated due to the ambient air being in contact with the mesh layer 30 on the surface of the absorbent layer 40. Thus, excess heat from the body is gradually dissipated.

Figure 6:
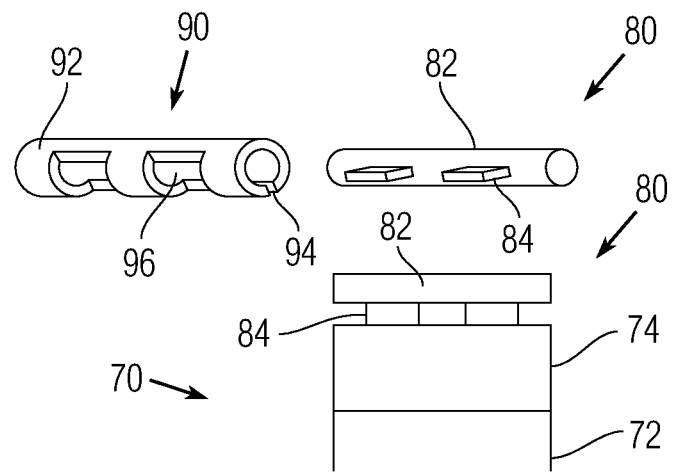
FIG. 6 depicts a band attaching mechanism, according to an example of the present disclosure.

In an example, the cooling system 100 can be connected to a band 70. The band 70 includes a first portion 72 that is made of a material that can conform to a user's wrist. For example, the first portion can be made of a polymeric material, such as plastic, rubber, nylon, or a chain. The band 70 can also include a second portion 74 that can, at one end, securely receive an end of the first portion 72 and at the other end can securely receive a male connector 80. The male connector 80 can include a body 82 and at least one protrusion 84, such as two protrusions. The at least one protrusion 84 can be secured to one end of the second portion 74 of the band 70, such that the body 82 of the male connector 80 extends away from the end of the band 70, as shown in FIG. 6.

In an example, to secure the male connector 80 to its corresponding female connector 90, the male connector 80 can be aligned with the body 92 of the female connector 90, such that the body 82 can be inserted into the slotted opening 94 of the body 92. Additionally, the body 92 of the female connector 90 can include a second opening or a second set of openings 96, which allow the at least one protrusion 84 to rotate around its axis to allow a user to remove or place the cooling system 100 on her wrist. The female connector 90 can be secured to the cooling system 100.

Figure 7:
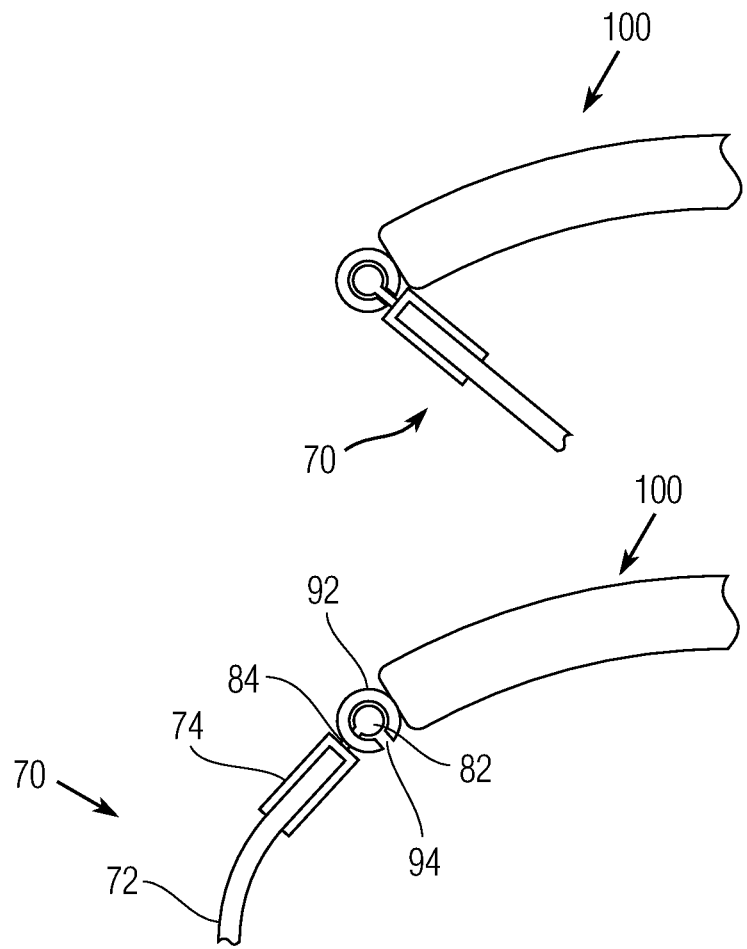
FIG. 7 depicts the band attaching and rotating mechanism of FIG. 6, according to an example of the present disclosure.

FIG. 7 illustrates how the band 70 is connected to the cooling system 100 and how the band can rotate with respect to the cooling system 100. As shown in FIG. 7, once body 82 has been inserted into the body 92, the second set of openings 96 (not visible in FIG. 7) allow the protrusion 84 rotatably connecting the band 70 to the female connector 90 to rotate freely.

EXAMPLES

Figure 8:
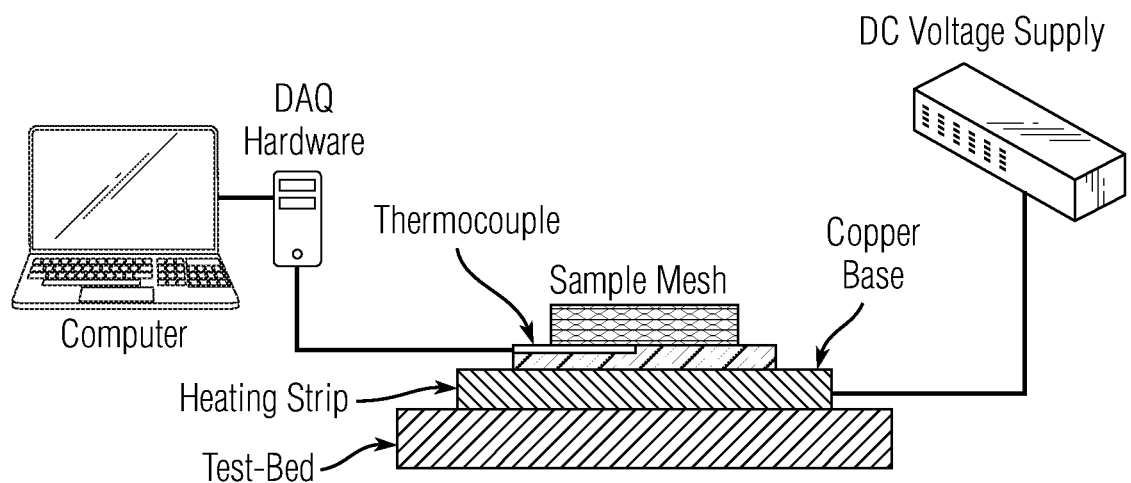
FIG. 8 depicts the schematic setup of an experiment performed on the body cooling system, according to an example of the present disclosure.

An experiment was conducted using the setup shown in FIG. 8. The setup included placing a copper plate onto the heating strip. The copper plate here acted as the "human skin," one surface of which is heated and the other surface is cooled.

A power supply was connected to the heat strip. Upon application of voltage to the heating strip, the copper plate reached a steady-state temperature. To modulate the temperature to the desired temperature for this experiment, the voltage on the DC power supply was adjusted, and a period of time was passed for the temperature response of the copper plate to stabilize. The thermocouple value was then recorded.

Upon stabilization of the temperature, the cooling system was placed on top of the copper plate. For the purposes of this experiment, for testing the mesh/the fabric samples, the absorbent layer/material was placed between two hydrophobic mesh. The absorbent layer was then soaked with water and placed on top of the copper plate.

A description of the materials and devices used in this experiment are described in Table 1, below.

TABLE 1

Testing Set-Up Device and Materials

| Item | Description |
| --- | --- |
| Lab-view Software | Data acquisition software - collects and store temperature values for future analysis |
| cDAQ - 9171 | Analog - Digital Signal converter, inputs raw voltage, outputs waveform to computer |
| Teflon Platform | Large "stage" for test samples to be placed on, offers thermal isolation from table |
| MASTECH DC Power Supply HY3010E-3 | The power supply which provides an accurate voltage output to heating strip |
| All Flex Flexible Heat Strip | Resistive heating element, the temperature can be modulated via voltage. Replicates the "skin" heat source |

TABLE 1-continued

Testing Set-Up Device and Materials

| Item | Description |
| --- | --- |
| 10 mL Samples | Set-volume beakers (made of different materials) to explore the effects of ONLY liquid on cooling the substrate |
| Mesh/Fabric Samples | Combination of a mesh and fabric to simulate the end product. |
| Copper Plate | Serves as a base for the sample, thermocouple, and heating strip |
| Thermocouple | Surface-mount thermocouple, reading temperature values on the copperplate |

For comparison purposes, in addition to a bear mesh, two different mesh materials were used. The first mesh (Mesh 1) was a 12 mesh Cu, 0.023" wire diameter. The second mesh (Mesh 2) was a 16 mesh CU, 0.011" wire diameter. In both cases, the hydrophilic membrane filter/coating was a 47 mm diameter, 0.22 µm pore size. The characteristics of Mesh 1 and Mesh 2 are shown in Table 2 below.

TABLE 2

Characteristics of Mesh 1 and Mesh 2 in Different When Wet and Dry

|  | Bare membrane | Mesh 1 | Mesh 2 |
| --- | --- | --- | --- |
| Dry mass, $m_{dry}$ (g) | 0.0314 | 1.5477 | 0.6581 |
| Wet mass, $m_{wet}$ (g) | 0.0760 | 1.6283 | 0.7444 |
| Mass of liquid (g) | 0.0446 | 0.0806 | 0.0863 |

Figure 9:
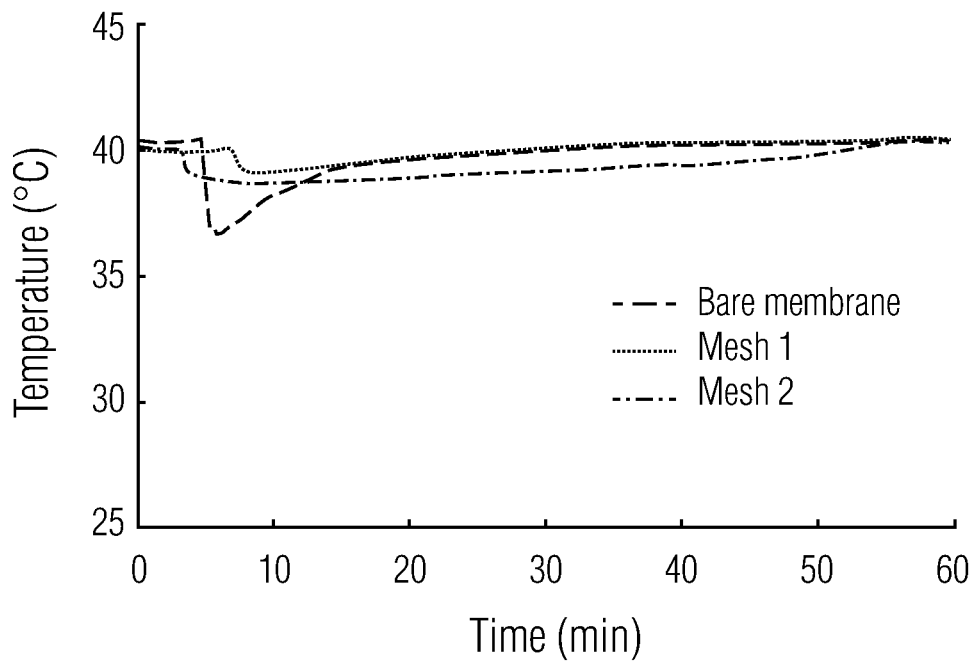
FIG. 9 depicts a graph showing the results of the temperature versus time with respect to the mesh material, according to an example of the present disclosure.

FIG. 9 illustrates the results of the temperature versus time of each different mesh. The characteristics of the absorbent layer used in the experiment are shown in Table 3, below.

TABLE 3

Characteristics of the absorbent layer containing water and containing ethanol.

|  | Water | Ethanol |
| --- | --- | --- |
| Dry mass, $m_{dry}$ (g) | 0.1735 | 0.1623 |
| Wet mass, $m_{wet}$ (g) | 1.6012 | 1.4823 |
| Mass of liquid (g) | 1.4277 | 1.3200 |

Figure 10:
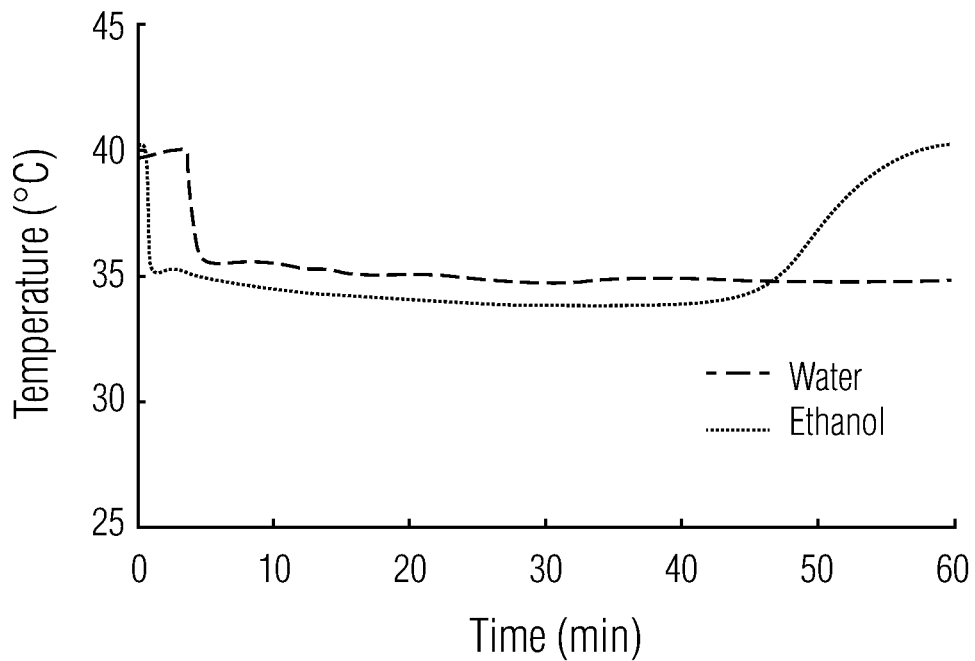
FIG. 10 depicts a graph showing the results of the temperature versus time with respect to the absorbent layer having water, according to an example of the present disclosure.
Figure 11:
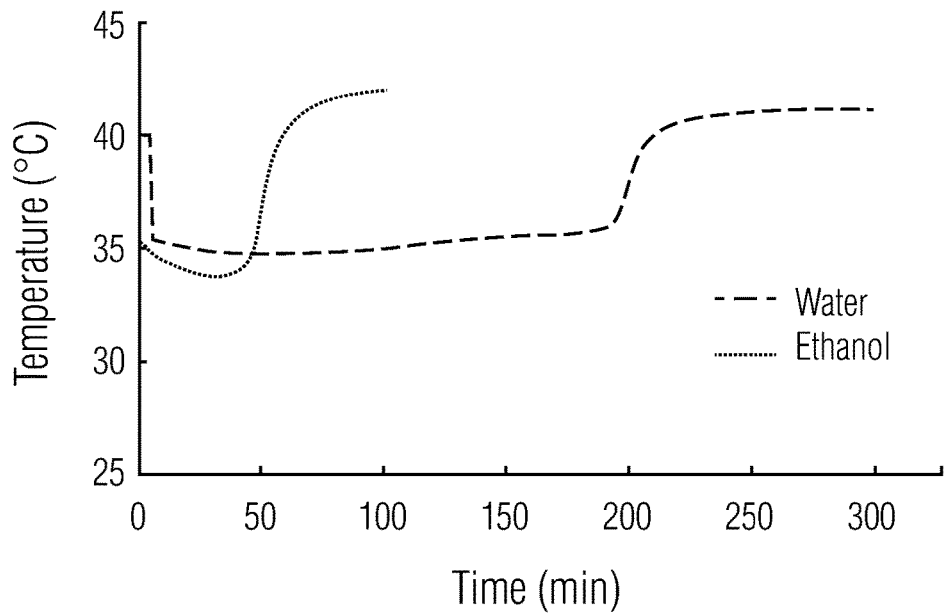
FIG. 11 depicts a graph showing the results of the temperature versus time with respect to the absorbent layer having ethanol, according to an example of the present disclosure.
Figure 12:
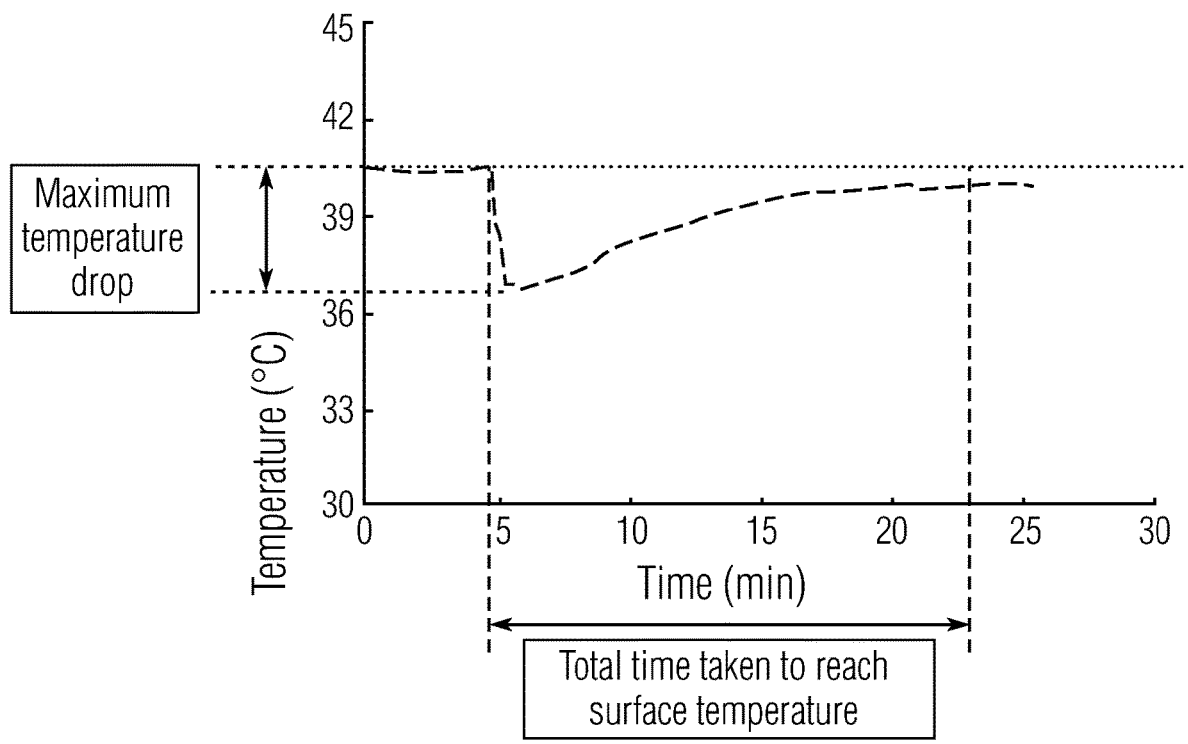
FIG. 12 depicts a graph showing the result of the maximum temperature drop and the total time taken to reach the surface temperature, according to an example of the present disclosure.

FIGS. 10 and 11 illustrate the results of the temperature versus time of each different liquids used in the absorbent layer. Additionally, FIG. 12 illustrates the result of the maximum temperature drop and the total time taken to reach the surface temperature.

From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The scope of this disclosure is to be broadly construed. It is intended that this disclosure disclose equivalents, means, systems, and methods to achieve the devices, activities and mechanical actions disclosed herein. For each device, article, method, mean, mechanical element or mechanism disclosed, it is intended that this disclosure also encompass in its disclosure and teaches equivalents, means, systems, and methods for practicing the many aspects, mechanisms and devices disclosed herein. Additionally, this disclosure regards a coating and its many aspects, features, and elements. Such a device can be dynamic in its use and operation, this disclosure is intended to encompass the equivalents, means, systems, and methods of the use of the device and/or article of manufacture and its many aspects consistent with the description and spirit of the operations and functions disclosed herein. The claims of this application are likewise to be broadly construed.

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

We claim:

1. A body cooling system configured to be worn as a device by an individual, the body cooling system comprising:
a housing including a top portion, side portions, and a bottom portion, wherein the top portion and the bottom portion each include at least one opening and wherein the housing includes an ornamental design;
a mesh layer including a hydrophobic coating; and
an absorbent layer at least partially surrounded by the mesh layer,
wherein the housing is configured to retain the mesh layer and the absorbent layer,
wherein the hydrophobic coating of the mesh layer is on a side of the mesh layer facing the absorbent layer, and
wherein the at least one opening in the bottom portion of the housing includes at least a portion of at least one of: the mesh layer and the absorbent layer.

2. The body cooling system of claim 1, wherein the at least one opening in the top portion of the housing is in fluid contact with ambient air.

3. The body cooling system of claim 1, wherein the hydrophobic coating comprises silane.

4. The body cooling system of claim 3, wherein the silane is Trimethoxy(1H,1H,2H,2H-perfluorodecyl)silane.

5. The body cooling system of claim 1, wherein the mesh layer includes a mesh size of from 50×50 mesh to 250×250 mesh.

6. The body cooling system of claim 1, wherein the mesh layer includes a mesh size of 100×100 mesh.

7. The body cooling system of claim 1, wherein the mesh layer includes from 10% opening to 50% opening.

8. The body cooling system of claim 1, wherein the mesh includes at least 30% opening.

9. The body cooling system of claim 1, wherein the mesh layer is made of a material having anti-bacterial characteristics.

10. The body cooling system of claim 1, wherein the mesh layer is made of at least one of silver, copper, gold, aluminum, magnesium, sodium, graphite, tungsten, beryllium, zinc, nickel, steel, tantalum, stainless steel, and alloys thereof.

11. The body cooling system of claim 1, wherein the mesh layer is made of 304 stainless steel mesh.

12. The body cooling system of claim 1, wherein the absorbent layer has 100% absorbing capacity.

13. The body cooling system of claim 1, wherein the absorbent layer comprises a material made of polypropylene or hydrogel.

14. The body cooling system of claim 1, wherein the absorbent layer comprises at least one of polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

15. The body cooling system of claim 1, wherein the device is in the form of a bracelet or a neckless.

16. The body cooling system of claim 1, wherein the hydrophobic coating is on both sides of the mesh layer.

\* \* \* \* \*